(12) United States Patent
Coppi (10) Patent No.: US 7,384,412 B2
(45) Date of Patent: *Jun. 10, 2008

(54) ENDOVASCULAR SYSTEM FOR THE TREATMENT OF STENOSES OF THE CAROTID AND CATHETER FOR THIS SYSTEM

(75) Inventor: Gioacchino Coppi, Modena (IT)

(73) Assignee: Invatec S.r.l. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/190,823

(22) Filed: Jul. 28, 2005

(65) Prior Publication Data

US 2005/0273051 A1    Dec. 8, 2005

Related U.S. Application Data

(62) Division of application No. 10/601,545, filed on Jun. 24, 2003, now Pat. No. 7,083,594, which is a division of application No. 09/857,107, filed as application No. PCT/EP99/09295 on Nov. 30, 1999, now Pat. No. 6,595,953.

(30) Foreign Application Priority Data

Dec. 3, 1998  (IT)  .............................. SV98A0070

(51) Int. Cl.
*A61M 29/00*  (2006.01)

(52) U.S. Cl. ................................. 604/101.04

(58) Field of Classification Search .............. 604/96.01, 604/101.01, 98.01, 99.01, 101.04, 101.05, 604/103.04, 101.03, 101.02
See application file for complete search history.

(56) References Cited

U.S. PATENT DOCUMENTS

| 2,642,874 A | | 6/1953 | Keeling |
| 2,936,760 A | * | 5/1960 | Gants .................... 604/101.03 |
| 3,509,884 A | | 5/1970 | William |
| 4,771,777 A | | 9/1988 | Horzewski et al. |
| 4,840,690 A | | 6/1989 | Melinyshyn |
| 5,135,484 A | | 8/1992 | Wright |
| 5,250,060 A | | 10/1993 | Carbo et al. |
| 5,328,471 A | | 7/1994 | Slepian |
| 5,380,284 A | | 1/1995 | Don Michael |
| 5,462,529 A | * | 10/1995 | Simpson et al. ....... 604/101.04 |
| 5,628,719 A | | 5/1997 | Hastings |

(Continued)

FOREIGN PATENT DOCUMENTS

WO    WO 95/05209    2/1995

(Continued)

*Primary Examiner*—Kevin C. Sirmons
*Assistant Examiner*—Catherine N. Witczak
(74) *Attorney, Agent, or Firm*—Nixon & Vanderhye PC (57) ABSTRACT

A catheter, in particular for endovascular applications, including a long and flexible, hollow, tubular body having an insertion end and a connection end intended to remain outside the body. The catheter includes in the insertion end at least two elements which are expandable/contractible by means of external operations. Those elements are located at a distance from each other, one upstream and the other downstream of a given section of a vessel. With the catheter it is possible to operate in the section between the two expandable elements and, if necessary, in the intermediate arterial branch which, on account of the two elements upstream and downstream, will have a zero flow.

6 Claims, 4 Drawing Sheets

U.S. PATENT DOCUMENTS

| | | | |
|---|---|---|---|
| 5,833,650 A * | 11/1998 | Imran | 604/509 |
| 6,146,370 A | 11/2000 | Barbut | |
| 6,464,664 B1 | 10/2002 | Jonkman | |
| 6,533,800 B1 | 3/2003 | Barbut | |
| 6,595,953 B1 * | 7/2003 | Coppi et al. | 604/96.01 |
| 6,623,471 B1 | 9/2003 | Barbut | |
| 6,626,886 B1 | 9/2003 | Barbut | |
| 7,083,594 B2 * | 8/2006 | Coppi | 604/101.01 |
| 2004/0039331 A1 | 2/2004 | Coppi et al. | |
| 2004/0127885 A1 | 7/2004 | Barbut | |

FOREIGN PATENT DOCUMENTS

| | | |
|---|---|---|
| WO | WO 98/38930 | 9/1998 |
| WO | WO 99/66977 | 12/1999 |

* cited by examiner

ENDOVASCULAR SYSTEM FOR THE TREATMENT OF STENOSES OF THE CAROTID AND CATHETER FOR THIS SYSTEM

CROSS-REFERENCE TO RELATED APPLICATIONS

This application is a Division of U.S. application No. 10/601,545 filed Jun. 24, 2003 now U.S. Pat. No. 7,083,594, which is a Division of U.S. application Ser. No. 09/857,107 filed Jul. 17, 2001, now U.S. Pat. No. 6,595,953 which is the U.S. national phase of international application No. PCT/EP99/09295 filed Nov. 30, 1999, which designated the U.S., the entire disclosure of each of which is hereby incorporated by reference in this application.

BACKGROUND OF THE INVENTION

The invention relates to a catheter, in particular for endovascular applications, comprising a long and flexible, hollow, tubular body having an insertion end and a connection end intended to remain outside the body.

In the medical field it is known that there exists the need to carry out suitable procedures for the treatment of vessels which are obstructed—at least over part of their diameter—by constrictions, or so-called "stenoses", arteriosclerotic plaques with or without superimposed thrombi, or the like, in order to restore the complete accessibility and functionality thereof. Said stenoses may hinder or even prevent the normal flow of substances which physiologically pass through the vessels. In particular in the case of the carotid artery, said stenoses may hinder or even prevent the normal flow of blood towards the organs in the head such as, for example, the brain and the eyes. Said stenoses may also release fragments of plaque or thrombi with the possibility of serious embolisms affecting the abovementioned organs.

Normally these types of pathologies are dealt with by means of external surgery. Said surgery involves the incision of the skin and the underlying layers and isolation of the section of artery affected by the stenosis; it also involves clamping the artery itself, which is performed upstream and downstream of the stenosis so as to block the circulation temporarily. In particular, in the case of the carotid artery, said clamping is normally performed upstream and downstream of the carotid bifurcation, i.e. on the common carotid, on the internal carotid and on the external carotid. At this point it is envisaged operating on the section affected by the stenosis using the appropriate procedures which envisage removal of the obstructing plaque through the opening of the artery section concerned, which is then carefully cleaned and sewn up again directly or by means of application of a prosthetic widening tissue (called "patch"). The surgical method involves, however, closure of the section of the carotid artery operated on with interruption of the blood flow for a period of time of about 15-30 minutes. During this period of time, the flow of blood to the brain is compensated for by the flow coming from other arteries directed towards the brain.

In 10-15% of cases this compensation of the blood flow is not sufficient and, after just 9 minutes of clamping, serious damage to the brain may occur. To avoid this, it is necessary to carry out extremely rapid operations with the risk of imprecision, or apply special devices consisting of temporary bridges (or "shunts") which are applied downstream of the section of carotid artery which is obstructed. These devices, however, cause an obstruction in the operating zone and may cause complications and, for these reasons, are used only if absolutely necessary. In order to identify the cases where shunts are required, numerous systems have been developed for monitoring the state of the brain or the cerebral blood flow. These systems are not devoid of errors or inaccuracies, so that many surgeons use the method of brain monitoring while operating on the patient in the conscious state and under a local anaesthetic. This method, which is the safest for avoiding brain damage during the operation, has the drawback that it subjects the patient to a great deal of stress and often is very painful, in particular in the case of patients with particular anatomical forms ("bull neck") or who have carotids affected by lesions or carotid bifurcations which are situated very high in the neck. The operation also involves the possibility of damage to the nerves in the neck, in particular in the case of repeated operations or necks subjected to radiotherapy, with unpleasant post-operative consequences.

In view of the above situation, for several years now there has been the need to provide a new instrument for therapeutic treatment which allows treatment of pathologies such as those described or similar pathologies, using procedures which are less invasive or not invasive at all, in order to reduce as far as possible the risks for the patient, associated with a surgical operation. For this purpose, in about the year 1980, Matias was the first person to transfer the techniques of endoluminal dilation of the peripheral arteries to the carotid arteries. These techniques involve positioning a guide wire beyond the stenoses. A catheter eguipped with an inflatable element (commonly called a "balloon") is then passed along the guide wire and the inflatable element is expanded in the region of the stenosis in order to dilate it. This method has been successful, but also involves many complications due to thromboses or embolisms.

The results have improved with the use of elements, called "stents", which consist in tubular shaped meshwork structures which have the task of supporting the dilated section, holding in place the thrombus and plaque fragments. Despite this, the number of unsuccessful results have still been high. In order to avoid embolisms during the procedure, guide wires provided with a "balloon" to be applied inside the internal carotid artery, or a supporting catheter provided with an expandable element (or "balloon") to be applied to the common carotid artery, have beer developed. These methods, however, are unable to prevent possible embolisms during the endoluminal manoeuvre since they do not provide protection during the initial stages of insertion of the guide wires ("Teron" method) and moreover they do not exclude the flow towards the brain through the external carotid artery.

SUMMARY OF THE INVENTION

The object of the present invention is therefore that of providing a catheter which is able to overcome these drawbacks by means of occlusion or clamping involving the inflation of expandable elements (or "balloons") simultaneously inside the common carotid artery and inside the external carotid artery. This catheter must also have an operating channel which allows the stenotic artery sections to be dilated and the appropriate stents to be applied rapidly, sucking then inside the artery section concerned any embolism-producing material, thereby associating the safety of conventional surgery with the advantages of the endoluminal procedures.

The invention therefore has the aim of providing, by means of simple and low-cost measures, a catheter of the type described initially which allows:

exclusion of a section of a vessel from the blood flow, in order to block temporarily the circulation of the substances which physiologically pass through them, so as to be able to carry out any treatment or manoeuvre inside the said vessel section;

the abovementioned isolation and subsequent treatment using procedures which are invasive to a minimal degree or not at all, and in particular the possibility of insertion in loco by means of an extremely small incision inside an artery situated at a distance (such as, for example, the femoral artery);

elimination of the need for a surgical operation, thereby reducing the risks for the patient, said risks always being associated with treatment of the invasive type;

treatment of vessel sections which have undergone a previous surgical operation and/or reduction of the operating zone also in the case of a first operation;

provision of an instrument for treatment which is extremely simple to use;

reduction in the duration and the costs of the operation and the period of hospitalisation and convalescence of the patient, resulting in considerable savings in the associated maintenance costs.

The invention achieves the abovementioned objects by means of a catheter of the type described initially, comprising at the insertion end or distal end, at least two elements which are expandable/contractible by means of external operation.

Said expandable/contractible elements may be arranged at a distance from one another such that one is able to operate upstream and the other downstream of a given section of a vessel or two different adjacent vessel sections.

Said expandable/contractible elements may be adapted, with regard to their diameters in the expanded condition, to the diameters of the vessels inside which they are to be positioned, so as to occlude them entirely and block temporarily the blood circulation in the section or sections concerned.

Said expandable/contractible elements located at the insertion end may be inflated/deflated by means of supply and discharge ducts provided in the thickness of the catheter wall. This solution allows the diameter of the catheter to be limited, facilitating insertion of the latter, and avoids occupying the internal central luminal duct, or operating channel, which is intended to convey the appropriate treatment means.

The catheter may have a hollow tubular shape with a larger initial diameter provided externally, in particular at the distal end, with a first inflatable/deflatable element, operation of which is performed via one of the ducts provided within the thickness of the catheter.

At least one of the other ducts provided within the thickness of the catheter may extend, over a certain length, into a second section of the catheter, of smaller diameter, which extends from the distal end of the larger-diameter section and terminates in a second inflatable/deflatable element, operation of which is performed via said duct.

The catheter comprises a further duct in the wall thickness, which emerges at the tip of the entire catheter, namely at the distal end of the second smaller-diameter section. This duct has the function of conveying the guide wire.

The hollow larger-diameter catheter section has a further central duct with a diameter suitable for conveying treatment means necessary for operating in the vessel section or sections comprised between the two inflatable/deflatable elements. Said treatment means may consist in balloon or stent catheters both of the self-expanding type and the type expandable by means of inflation, in which case the stent may be located at the distal end of an additional catheter of a suitable diameter and introduced via the central duct of the catheter according to the invention, so as to reach the vessel section inside which it must be applied.

The section comprised between the two inflatable/deflatable elements may have a length of the order of between a few cm and about 10 cm, i.e. substantially equivalent to the longitudinal extension, for example, of stenoses in arterial vessels or the like or the section of a main vessel to be occluded and the first section of a bifurcation branch (as in the case of a common and external carotid), thus blocking any flow in the second dividing branch.

For particular applications, the two elements may be provided at distances different from those indicated above.

The catheter may have a first external larger diameter of the order of magnitude of about 12-13 French and in any case preferably not greater than 13-14 French (approximately 4 mm), while the second external smaller diameter may be of the order of magnitude of about 5 French (approximately 1.5 mm). For particular applications, diameters with measurements different from those indicated above may be envisaged.

The catheter may have, in the connection end or proximal end, an end-piece intended to remain outside the patient's body. Said end-piece may be provided with tubular elements, which are preferably rigid or semi-rigid, having the function of providing a connection to the individual ducts.

The catheter according to the present invention may be used advantageously in particular in an endovascular system for the treatment of stenoses of the carotid, in order to isolate an artery section inside which a stenosis is present, so as to block temporarily the blood flow inside the said vessel section. Said system may comprise the following steps:

positioning of a guide wire so that, when passing in particular inside the common carotid, its distal end is arranged inside the internal carotid;

insertion of the catheter on the guide wire, through the respective duct provided in the thickness of the catheter wall;

positioning of the catheter so that the end of the smaller-diameter extension is arranged, with respect to the direction of the blood flow, in particular in the external carotid and the larger-diameter end is arranged in particular inside the common carotid;

inflation of the two expandable/contractible elements via the two respective ducts provided in the thickness of the catheter wall;

treatment of the stenosis in the internal carotid by means of insertion of the appropriate instruments or treatment (guides, balloon catheters, stents, aspirators, angioscopic instruments, IVUS, devices for thrombolysis, catheters for angiographic checks, etc.) through the central duct;

aspiration through the central duct 2 of possible residues deriving from catheter expansion;

deflation of the two expandable/contractible elements via the two respective ducts provided in the thickness of the catheter wall;

final monitoring;

extraction of the catheter and the guide wire.

All the abovementioned steps may be performed with continuous visual monitoring, thanks to one of the well-known existing techniques. In this connection, the tubular body of the catheter may comprise radiopaque markers for locating and identifying the said catheter.

As a result of the series of measures described above it is possible to provide, using simple and low-cost means, a catheter which allows:

- isolation of a section of a vessel so as to prevent temporarily the flow of the substances which physiologically pass through it, so as to be able to carry out any treatment inside this vessel section;
- the abovementioned isolation and subsequent treatment using procedures which are only slightly invasive or not at all invasive, and in particular the possibility of insertion in loco by means of an extremely small incision situated at a distance (such as for example the femoral artery);
- elimination of the need for a surgical operation, thereby reducing the risks for the patient, said risks always being associated with treatment of the invasive type;
- treatment of vessel sections which have undergone previous surgery and/or reduction of the operating zone also in the case of a first operation;
- provision of an instrument for treatment which is extremely simple to use;
- reduction in the duration and the costs of the operation and the period of hospitalisation and convalescence of the patient, resulting in considerable savings in the associated maintenance costs.

The additional features and any improvements of the invention will be described in the sub-claims.

BRIEF DESCRIPTION OF THE DRAWINGS

The characteristic features of the invention and the advantages arising therefrom will emerge more clearly from the following detailed description of the accompanying figures in which.

DETAILED DESCRIPTION

With reference to the figures, and at the moment particularly to FIGS. 1-4, a catheter according to the invention comprises a long, hollow, flexible tubular body 1. The tubular body 1 may comprise one or more tubular bodies, but in the preferred embodiment it comprises a single tubular element which has a central luminal duct 2 which extends from a connecting end, known as the proximal end 3, to an insertion or distal end 4.

Figure 1:
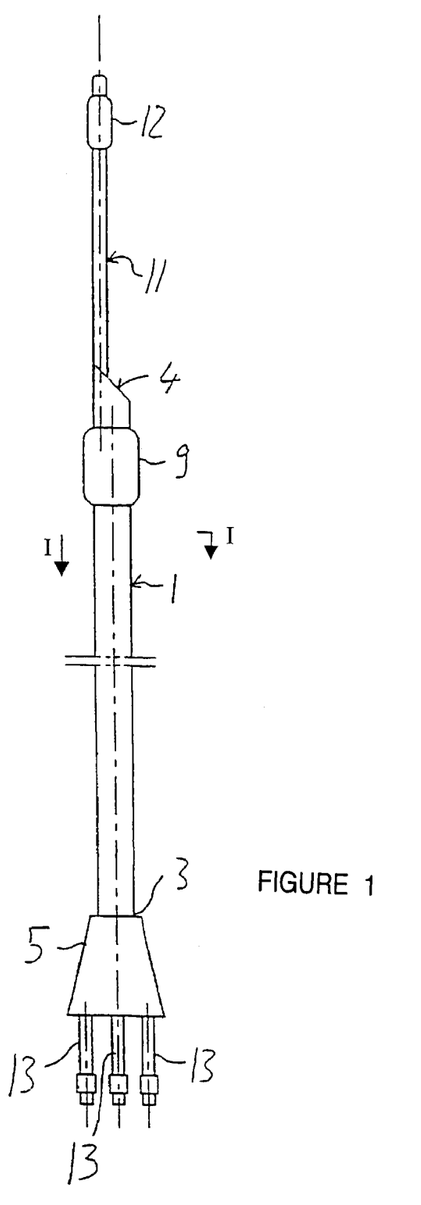
FIG. 1 shows a side view in a preferred embodiment of the catheter according to the invention.

The tubular body 1 may be made, for example, by means of extrusion of a small and flexible material such as nylon, polyurethane, urethane, polyethylene, polyvinyl chloride (PVC), polyamides or the like, which allows the tubular body 1 to bend for easy positioning inside the vessel inside which the said body must be positioned.

The external diameter of the tubular body 1 may be of the order of about 10-13 French (about 3-3.9 mm), and in any case preferably not greater than 13-14 French (3.9-4.2 mm), but may vary depending on the specific requirements.

Figure 2:
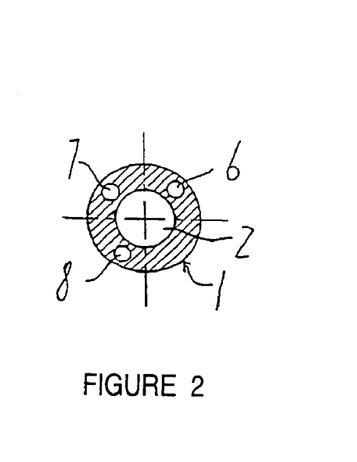
FIG. 2 shows an enlarged cross-sectional view of the catheter according to FIG. 1, along the line I-I, a further catheter being inserted inside the central duct.

The central luminal duct 2, or operating duct, has a diameter preferably not greater than 7 French (2.1 mm).

In the proximal end zone 3, the catheter has a connecting end-piece 5 which has a diameter greater than that of the tubular body 1 and which is intended to remain outside the patient's body.

Three ducts 6, 7 and 8, which have substantially the same diameter as each other, are provided in the thickness of the wall of the tubular body 1, but, for further applications, a different number of ducts may be provided, if necessary also with diameters which are different from each other.

Figure 3:
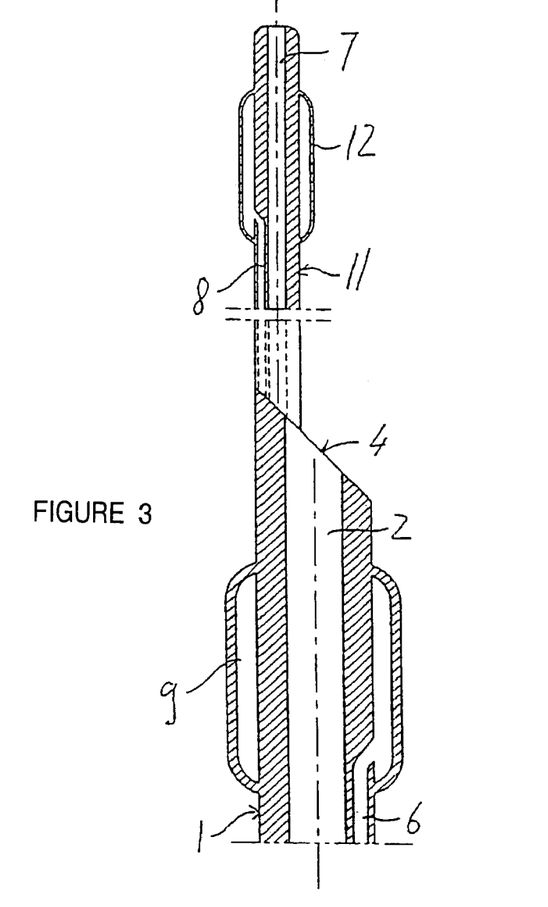
FIG. 3 shows an enlarged longitudinally sectioned view of the catheter according to FIG. 1, with the inflatable/deflatable elements in the non-expanded condition.

The first duct 6 extends from the proximal end 3 and emerges inside a first inflatable/deflatable element 9 which can be actuated by means of the duct 6 itself. Said first inflatable/deflatable element is provided in the immediate vicinity of the distal end 4 and basically consists of a balloon 9 which is applied is outside the wall of the tubular body 1 or is formed integrally with the latter. The diameter of said first balloon 9 in the expanded condition is such as to fit perfectly the internal diameter of the vessel for which it is intended, in particular the common carotid 10, in order to block temporarily the blood flow.

The second catheter 7 extends from one end to the other of the catheter, including that of the smaller-diameter extension, and forms the channel for the introduction of a guide wire, The third duct 8 extends from the proximal end 3 and extends beyond the distal end 4 by means of an extension 11 with an external diameter which is considerably smaller than that of the tubular body 1, in particular by about 5 French (approximately 1.5 mm). Said third duct emerges inside a second inflatable/deflatable element 12 located at the distal end of the extension 11. Said second element consists of a balloon 12 which is inflatable/deflatable by means of the duct 8 itself and may be applied to the distal end of the extension 11 or formed integrally therewith.

The diameter of said second balloon 12, in the expanded condition, is such as to fit perfectly the internal diameter of a vessel inside which said balloon is intended to be applied, in particular the external carotid 210, in order to block temporarily the flow of the blood.

The two balloons 9 and 12 are provided at a distance of about 10 cm from each other, but may be provided at different distances depending on the specific requirements.

The balloons 9 and 12, when not inflated, can also be comprised within the profile of the catheter portion or to which they are fitted.

The end-piece 5, at the proximal end 3 is provided with small rigid or semi-rigid pipes 13 for connecting each duct 6, 7 and 8 and the associated apparatus. Said apparatus may consist, for example, of means for inflating/deflating the balloons 9 and 12 by means of the ducts 6 and 8 and guide wires passing through the duct 7. The part connecting the main lumen of the catheter may have a removable valve and a lateral header.

Figure 4:
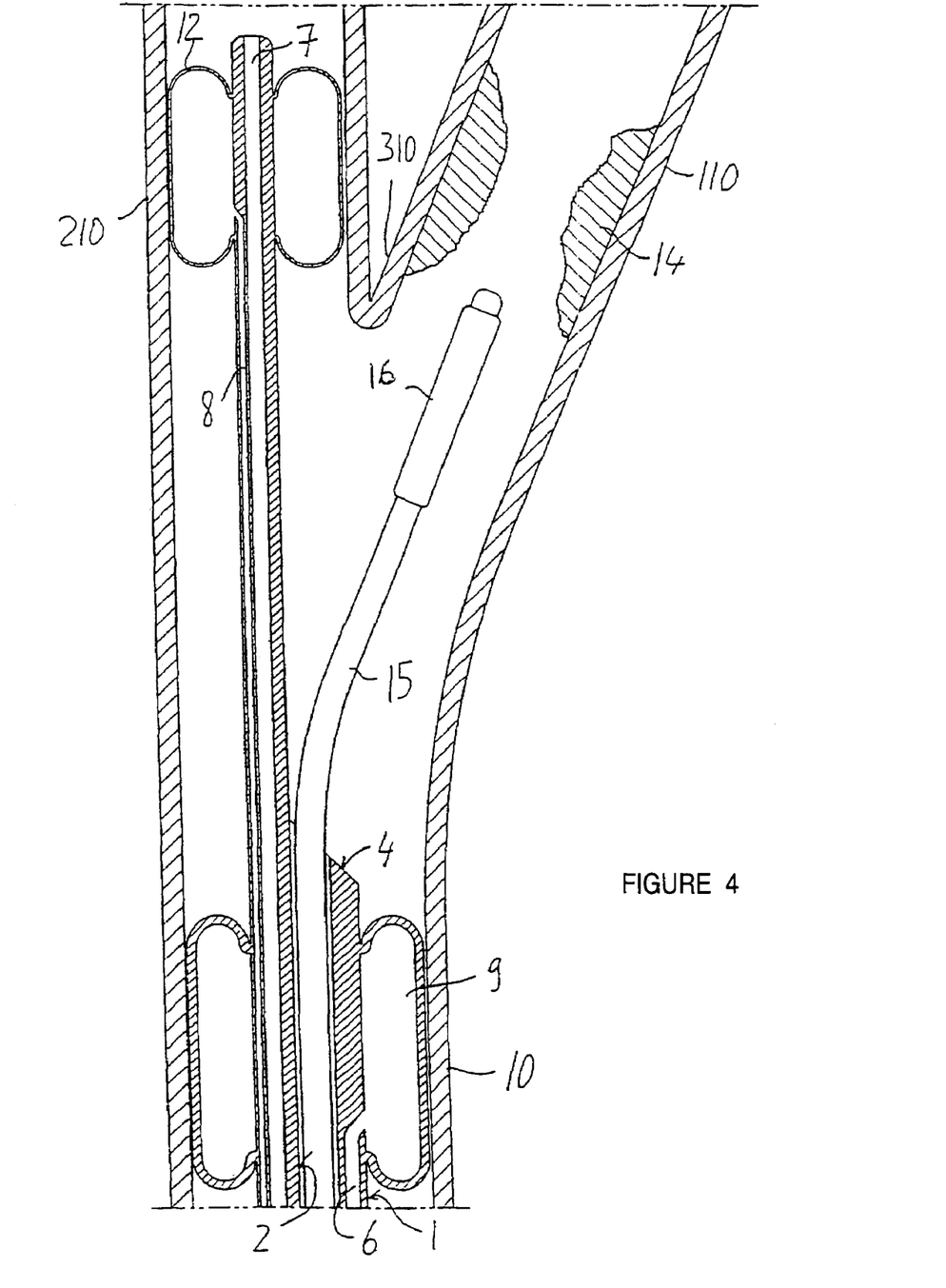
FIG. 4 shows a longitudinally sectioned view of a carotid artery, with the catheter in position and the inflatable/deflatable elements in the expanded condition.

With particular reference to FIG. 4, this shows a carotid artery in the zone close to the carotid bifurcation 310. The carotid shown has a stenosis 14 in the internal carotid section 110. The figure shows in detail the endovascular system for non-invasive treatment of the stenosis 14.

After positioning the catheter in the zone concerned via the femoral artery, with the aid of a guide wire and known observation means, the first balloon 9 is arranged inside the common carotid 10, while the second balloon 12 is arranged inside the external carotid.

At this point the balloons 9 and 12 are inflated by means of the respective ducts 7 and 8 with the effect of blocking the blood flow flowing from the common carotid and the reflux flow from the eternal carotid and stopping the flow in the internal carotid, the ostium of which remains accessible.

Owing to the interruption of the blood flow, it is possible to operate on the internal carotid, while ensuring that there is no danger of embolisms being able to reach extremely delicate organs, such as the brain for example, via the internal carotid 110. Obstruction of the internal carotid is not necessary because the distal pressure in the region of the circle of Willis prevents any flow in the direction of the brain and, therefore, any embolism.

At this point, the actual treatment is performed by means of the central duct 2 which constitutes an actual operating duct. By means of this operating channel, it is possible to introduce without danger a guide into the internal carotid; the catheters 15 for dilation and application of the stent 16 are then introduced. After the vessel section affected by the stenosis has been dilated and reinforced with the stent in the appropriate manner, aspiration of any waste matter is performed, a check carried out by means of angiography or other means, and renewed aspiration performed, if necessary, thereby completing the treatment procedure.

This procedure may be easily implemented within safe time periods, also with regard to the 10% (ten percent) of cases involving patients who cannot tolerate clamping of the arteries (less than 5 minutes), as determined experimentally in normal endoluminal procedures.

Figure 5:
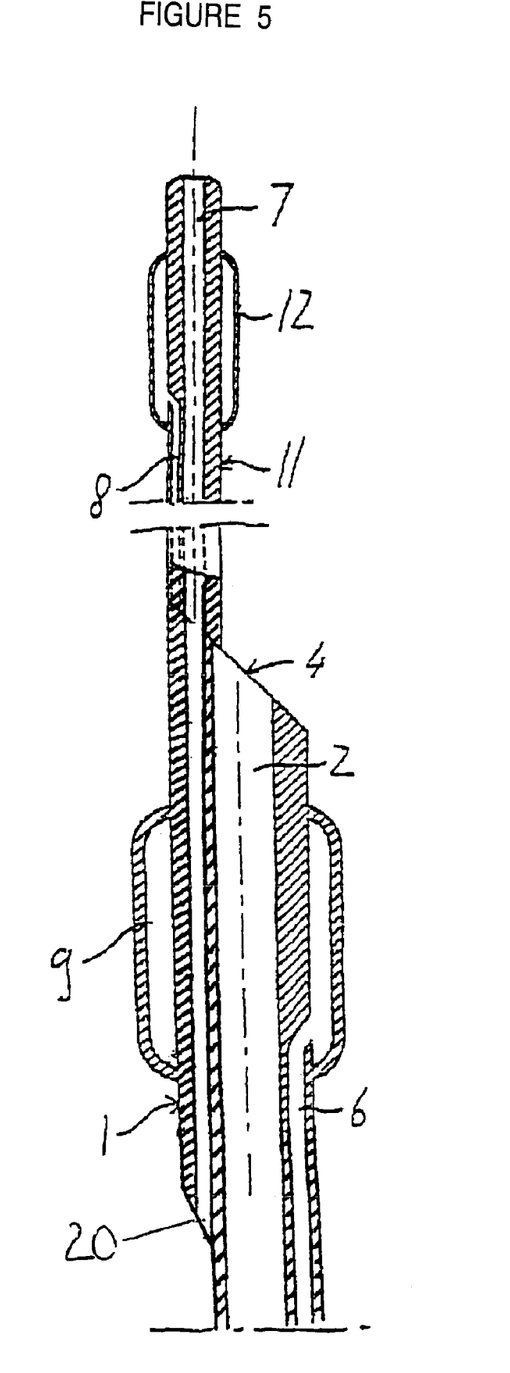
FIGS. 5 and 6 are longitudinal sectional views as that of FIG. 3, showing two slightly different embodiments of the catheter according to the invention.

The embodiment of FIG. 5 differs from that previously described in that the conduct 7 for the guide wire opens out of the tubular body 1 at a portion located between the proximal end 3 and the baloon 9, instead of extending up to the proximal end 3 of the catheter.

This embodiment makes the procedure for inserting the catheter very fast.

Figure 6:
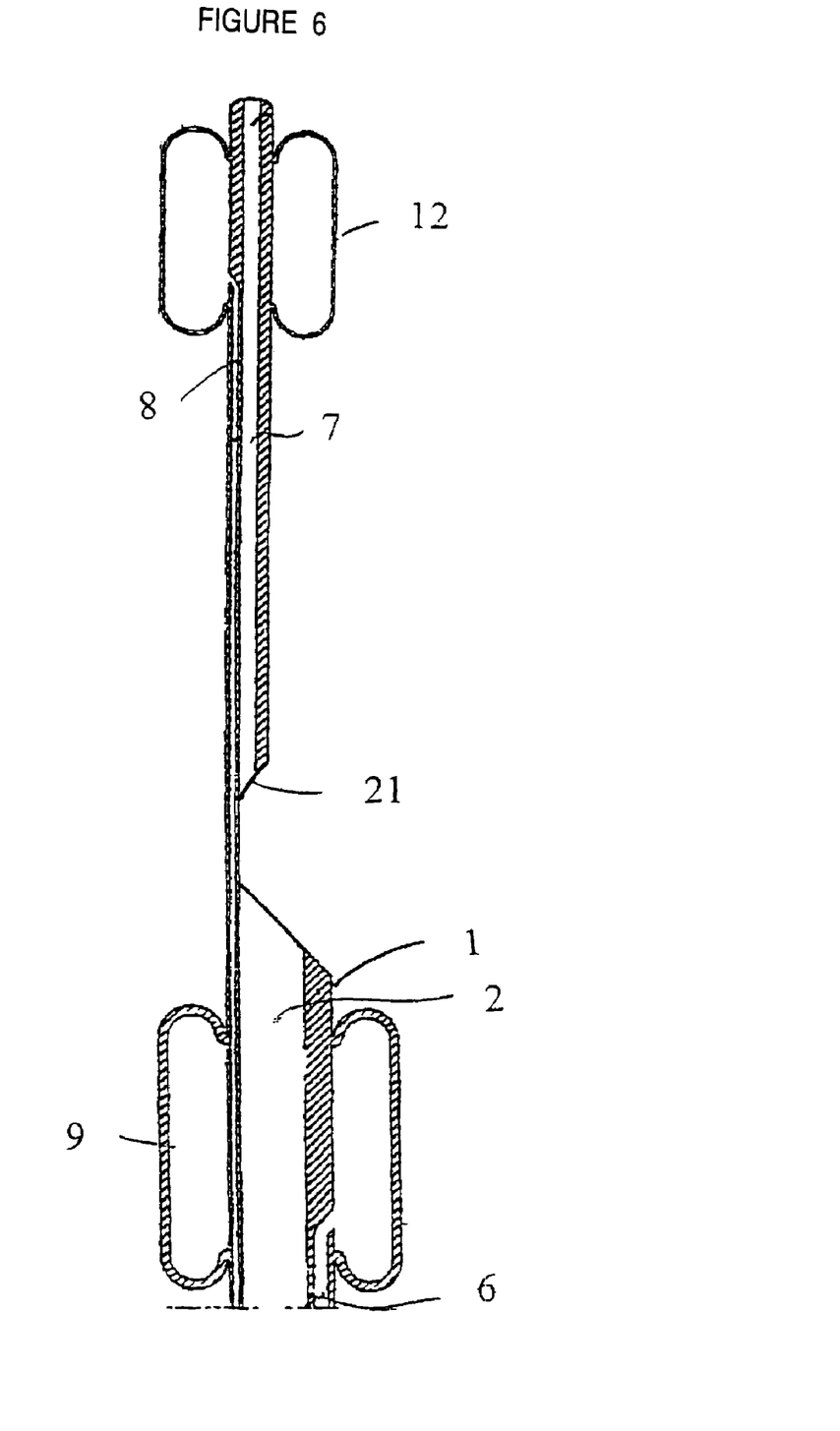

According to the embodiment shown in FIG. 6, the tubular body 1 does not provide for a lumen specifically designed for the passage of the guide is wire. This means that the conduct 7 for the guide wire is provided only in the distal portion of the catheter, and has an opening 21 located between the baloons 9 and 12. Therefore the guide wire runs within the central lumen 2 of the tubular body 1.

This embodiment allows to optimize the space available in the central lumen 2 of the tubular body 1.

If desired, one end of the balloons 9 can be positioned at the opening of the central duct 2.

Obviously, the invention is not limited to the embodiment and to the scope of treatment described and illustrated hitherto, but may be greatly varied and/or advantageously applied also in contexts different from the one described, without thereby departing from the basic principle described above and claimed below.

In particular, the previously described baloons 9 and 12 can be either compliant or non-compliant as well as the catheters and/or the baloons can be coated or uncoated.

The catheter according to the invention is preferably with soft and atraumatic tip and it can optionally have differentiated flexibility.

The invention claimed is:

1. A method of using a catheter comprising a long and flexible, hollow, single tubular body having an insertion end and a connection end intended to remain outside the body, and at the insertion end, at least two elements which are expandable/contractible by means of external operation and which are located on said single tubular body at a fixed distance from each other that is a predetermined and fixed length that does not change in use such as to be able to operate one upstream and the other downstream of a given section of a vessel, said expandable/contractible elements being adapted and/or being able to be adapted, with regard to their diameters in the expanded condition, to the diameters of the vessels inside which they are intended to be positioned, wherein the two elements located at the insertion end are inflatable/deflatable by means of supplying and discharge ducts which are provided inside the thickness of the catheter wall, wherein the single tubular body includes a main body having a first, larger diameter, provided on the outside with a first one of said elements which is inflatable/deflatable by means of one of the ducts provided in the thickness of the wall, wherein at least one other of the ducts inside the thickness of the wall extends, after a certain length, into an extension portion of the single tubular body having a second, smaller diameter and provided on the outside with a second one of said elements, and further comprising a central duct for conveying treatment means necessary for operating in the vessel section affected by stenosis, said central duct having a distal opening located between said expandable/contractible elements and defined through an inclined surface, wherein said extension portion has a through duct having a proximal opening located between said expandable/contractible elements and defined through an inclined surface, and wherein one of said expandable/contractible elements has a fully inflated diameter less than a fully inflated diameter of the other of said expandable/contractible elements, the method comprising the following steps:

insertion of the catheter inside the carotid artery via the femoral artery;

positioning of the catheter so that the end of the smaller-diameter extension is arranged, with respect to the direction of the blood flow, in the external carotid and the larger-diameter end is arranged inside the common carotid;

inflation of the two expandable/contractible elements via the two respective ducts provided in the thickness of the catheter wall;

operation on the stenosis of the internal carotid via insertion of the appropriate treatment instruments though the central duct;

aspiration through the central duct of possible residues deriving from catheter expansion;

deflation of the two expandable/contractible elements via the two respective ducts provided in the thickness of the catheter wall; and final monitoring and extraction of the catheter and the guide wire.

2. A method as in claim 1, wherein said smaller diameter expandable/contractible element is the most distal of said expandable/contractible elements.

3. A method as in claim 1, wherein said central duct extends along and includes a central axis of said single tubular body.

4. Catheter in particular for endovascular applications, comprising a long and flexible, hollow, single tubular body having an insertion end and a connection end intended to remain outside the body, and at the insertion end at least two elements which are expandable/contractible by means of external operation and which are located at a fixed distance from each other that is a predetermined and fixed length that does not change in use such as to be able to operate one upstream and the other downstream of a given section of a vessel, said single tubular body having a central duct for conveying treatment means necessary for operating in the vessel section affected by stenosis, said central duct having a distal opening located between said expandable/contractible elements and defined through and inclined surface, said expandable/contractible elements being adapted and/or being able to be adapted, with regard to their diameters in the expanded condition, to the diameters of the vessels inside which they are intended to be positioned, wherein the two elements located at the insertion end are inflatable/deflatable by means of supplying and discharge ducts which are provided inside the thickness of the catheter wall,     wherein the single tubular body includes a main body having a first, larger diameter, provided on the outside with a first one of said elements which is inflatable/deflatable by means of one of the ducts provided in the thickness of the wall, and an extension portion having a second, smaller diameter and provided on the outside with a second elements, and further comprising at least one additional duct for a guide wire, which emerges on the end side of the most distal end of the smaller-diameter extension, said duct for the guide wire extends only in the distal portion of the catheter and has an opening located between the inflatable/deflatable elements, and defined through an inclined surface, and wherein one of said expandable/contractible elements has a fully inflated diameter less than a fully inflated diameter of the other of said expandable/contractible elements.

5. Catheter as in claim 4, wherein said smaller diameter expandable/contractible element is the most distal of said expandable/contractible elements.

6. Catheter as in claim 4, wherein said central duct extends along and includes a central axis of said single tubular body.

* * * * *